United States Patent [19]

Karanewsky

[11] Patent Number: 4,804,770

[45] Date of Patent: Feb. 14, 1989

[54] PROCESS FOR PREPARING A KETO-PHOSPHONATE INTERMEDIATE USEFUL IN PREPARING HMG-COA REDUCTASE INHIBITORS

[75] Inventor: Donald S. Karanewsky, East Windsor, N.J.

[73] Assignee: E. R. Squibb & Sons, Inc., Princeton, N.J.

[21] Appl. No.: 188,564

[22] Filed: Apr. 29, 1988

[51] Int. Cl.[4] .............................. C07F 7/08; C07F 7/18
[52] U.S. Cl. .......................................................... 556/405
[58] Field of Search ........................................ 556/405

[56] References Cited
U.S. PATENT DOCUMENTS 4,093,641 6/1978 Plueddemann ...................... 556/405
4,721,800 1/1988 Chapman et al. .................... 556/405

Primary Examiner—Paul F. Shaver
Attorney, Agent, or Firm—Lawrence S. Levinson; Burton Rodney

[57] ABSTRACT

A process is provided for preparing the keto-phosphonate

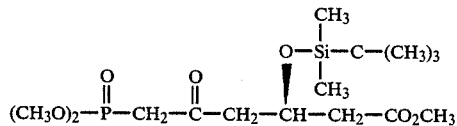

in enantiomerically homogeneous form, by reacting the anhydride

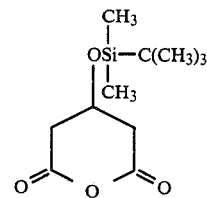

with S-α-methylbenzylamine to effect diastereoselective opening of the anhydride to give a mixture of amides

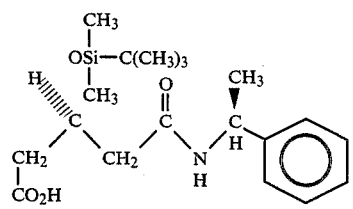

IVA and

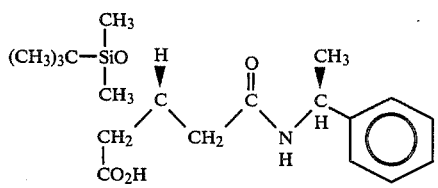

IVB separating the amides, for example, by frictional crystallization, and converting the desired amide IVA (which is obtained in high yield from the anhydride) to enantiomerically homogeneous ketophosphonate in high yield and on a large scale.

The so-formed ketophosphonate is useful in the synthesis of compactin as well as 7-substituted-(3,5-dihydroxy)-hept-6-enoic and -heptanoic acid HMG-CoA reductase inhibitors.

7 Claims, No Drawings

PROCESS FOR PREPARING A KETO-PHOSPHONATE INTERMEDIATE USEFUL IN PREPARING HMG-COA REDUCTASE INHIBITORS

FIELD OF THE INVENTION

The present invention relates to a process for preparing a keto-phosphonate in enantiomerically homogeneous form, which is useful in preparing HMG-CoA reductase inhibitors.

BACKGROUND OF THE INVENTION

Heathcock, JACS 107, 3731 (1985) and J. Med. Chem. 30, 1858 (1987) disclose the preparation of the keto-phosphonate A

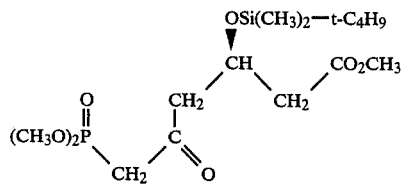

(which is used in the total synthesis of compactin) by separating by HPLC the diesters B-C

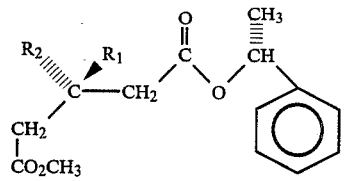

where in B, $R_1$ is $-OSi(CH_3)_2-t-C_4H_9$ and $R_2$ is H and in C, $R_1$ is H and $R_2$ is $-OSi(CH_3)_2-t-C_4H_9$ and then converting the isomer B to keto-phosphonate A in 5 steps to obtain an overall yield of 34%. Due to the difficulty of the HPLC separation of B and C, this technique can only be used to prepare relatively small quantities of keto-phosphonate A, for example, less than 0.5 g.

DESCRIPTION OF THE INVENTION

In accordance with the present invention, a process is provided for preparing the keto-phosphonate

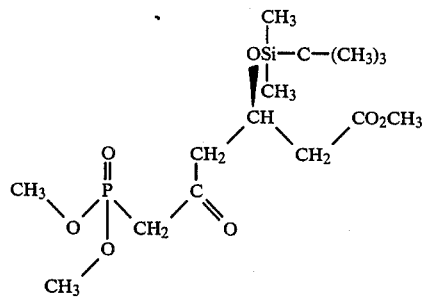

in enantiomerically homogeneous form which includes the steps of reacting the anhydride II

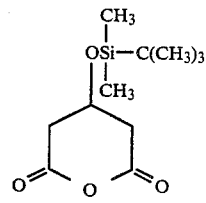

with S-α-methylbenzylamine III

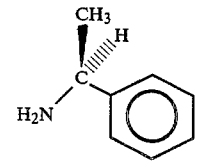

in the presence of a weak base such as an organic base like triethylamine, diisopropylethylamine or N-methyl morpholine and an inert organic solvent such as toluene or xylene at a reduced temperature to effect diastereoselective opening of the anhydride to give a mixture of amides IVA and IVB

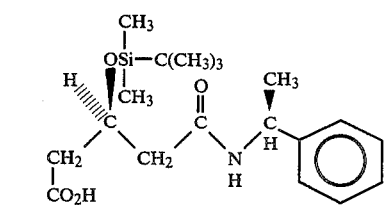
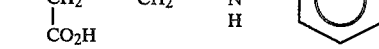

separating amides IVA from IVB, for example, by fractional crystallization and converting the desired amide IVA to enantiomerically homogeneous ketophosphonate I. The conversion of amide IVA to ketophosphonate I may be carried out by esterifying IVA by reacting IVA with an alkyl halide, such as methyl iodide in the presence of weak inorganic base such as $KHCO_3$, and an inert organic solvent such as dimethylformamide to form the amide-ester

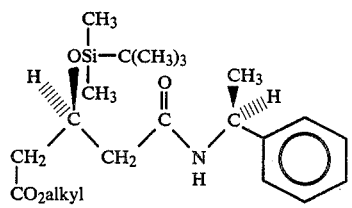

Amide-ester V in a solution of dry organic solvent, such as carbon tetrachloride maintained at a reduced temperature, under an inert atmosphere, such as argon, is treated with dinitrogen tetroxide in the presence of anhydrous sodium acetate to form the corresponding N-nitrosoamide which when heated in an inert solvent such as dioxane, undergoes a White rearrangement to release $N_2$ and form a mixture of acid VI and its corresponding 2-methylbenzyl ester

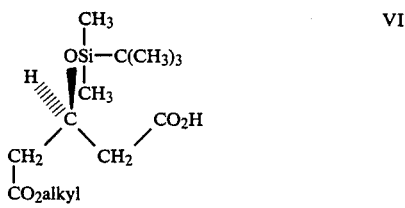

This mixture is treated with a hydrogen in the presence of a hydrogenation catalyst such as palladium on charcoal to convert the 2-methylbenzyl ester to acid VI. Acid VI is then converted to keto-phosphonate I by treating acid VI with the anion of dimethyl methylphosphonate (formed by treatment of dimethyl methylphosphonate with n-butyllithium) in an inert organic solvent such as tetrahydrofuran at reduced temperature under an inert atmosphere such as argon. The acid thus obtained is converted to keto-phosphonate I by treatment with diazomethane in ethyl ether.

The starting anhydride II may be prepared according to the procedure outlined in JOC 49, 3657 (1984) wherein a solution of imidazole in dry methylene chloride and t-butyldimethylsilyl chloride is treated with a solution of diethyl 3-hydroxyglutarate in methylene chloride to form silyl ether VII

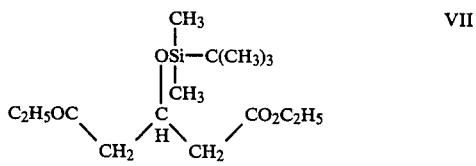

A solution of silyl ether VII in methanol is treated with a strong base such as sodium hydroxide under an inert atmosphere, such as argon, to form the corresponding disodium salt which is suspended in benzene and treated with acetic anhydride and refluxed under argon to form anhydride II.

In carrying out the process of the invention, the S-α-methylbenzyl amine III will be employed in a molar ratio to the anhydride II of within the range of from about 1:1 to about 2:1 and preferably from about 1:1 to about 1.1:1. The reaction of II and III will be carried out at a temperature of within the range of from about −100° to about 0° C. and preferably from about −100° to about −78° C.

In converting amide ester V to the N-nitrosoamide (which is subsequently converted to acid VI), dinitrogen tetroxide will be employed in a molar ratio to amide ester V of within the range of from about 1:1 to about 10:1 and preferably from about 1:1 to about 3:1. The reaction will be carried out at a reduced temperature of from about −25° to about 0° C. and preferably from about −10° to about 0° C.

The acid VI is reacted with the anion dimethyl methylphosphonate employing a molar ratio of dimethyl methylphosphonate anion to acid V of within the range of from about 5:1 to about 3:1 and preferably from about 3.5:1 to about 3:1, and a temperature of within the range of from about −100° to about −50° C. and preferably from about −100° to about −78° C.

The ketophosphonate I is useful in the synthesis of compactin (JACS 107, 3731 (1985)), mevinolin and for the preparation of 7-substituted-(3,5-dihydroxy)-hept-6-enoic and -heptanoic acid HMG-CoA reductase inhibitors, all of which are useful in inhibiting cholesterol biosynthesis. Other examples of such inhibitors of cholesterol biosynthesis are disclosed in J. Med. Chem. 28, 347 (1985); 29, 159 (1986); 29, 170 (1986); 29, 852 (1986) and 30, 1858 (1987).

The following Example represents a preferred embodiment in accordance with the method of the present invention. Unless otherwise indicated all temperatures are expressed in degrees Centigrade.

EXAMPLE (R)-6-(Dimethoxyphosphinyl)-3-[[(1,1-dimethylethyl)-dimethylsilyl]oxy]-5-oxohexanoic acid, methyl ester

A.

3-[[(1,1-Dimethylethyl)dimethylsilyl]-oxy]pentanedioic acid, diethyl ester [Ref.: JOC 49, 3657 (1984)]

To a solution of imidazole (40.85 g, 600 mmole) in dry $CH_2Cl_2$ (300 ml) was added dropwise a solution of t-butyldimethylsilyl chloride (45.2 g, 300 mmole) in dry $CH_2Cl_2$ (100 ml). After 15 minutes, the solution was treated dropwise over a 40 minute period with a solution of diethyl 3-hydroxyglutarate (40.8 g, 200 mmole) in $CH_2Cl_2$ (100 ml). After stirring at room temperature under argon for 18 hours, the mixture was washed with water and saturated NaCl solution, dried over $Na_2SO_4$ and evaporated. The crude product (73.04 g) was purified by chromatography on Merck silica gel (4000 ml), eluting with ethyl ether-hexane (1:9) to give title compound (~65 g, theory 63.6) as a colorless oil.

TLC: (ethyl acetate-hexane; 1:1) $R_f$=0.46 ($R_f$ of title compound=0.20).

$C^{13}$-NMR (15 MHz, $CDCl_3$)—5.02 ppm, 14.00, 17.77, 25.50, 42.51, 60.24, 66.28, 170.78.

B.

4-[[(Dimethylethyl)dimethylsilyl]oxy]dihydro-2H-pyran-2,6(3H)-dione

A solution of Part A silyl-ether (theory 63.6 g, 200 mmole) in methanol (200 ml) was treated with NaOH pellets (16.0 g, 400 mmole) and stirred at room temperature under argon for 18 hours. The cloudy yellow solution was evaporated to dryness and dried in vacuo to give the diNa salt as a pale yellow solid. The diNa salt (42.1 g) was suspended in benzene (400 ml), treated with acetic anhydride (200 ml) and refluxed under argon for 1.5 hours. The brown mixture was concentrated in vacuo and the residue partitioned between ethyl acetate and half-saturated $NaHCO_3$ solution. The organic phase was washed with half saturated $NaHCO_3$ and saturated NaCl solutions, dried over $Na_2SO_4$ and evaporated to give the crude title anhydride as a brown solid. The crude product was taken up in ethyl ether, treated with Darco (3 g), filtered through Celite and evaporated. The crystalline residue was triturated with cold hexane to give pure title anhydride (33.26 g, 68% overall from diethyl 3-hydroxy glutarate) as white plates, m.p. 77°–78° C., $C^{13}$-NMR (15 MHz, $CDCl_3$)—5.22 ppm, 17.64, 25.31, 38.88, 61.87, 165.26.

C.
(3S,1'S)-3-[[(1,1-Dimethylethyl)dimethylsilyl]oxy]-5-[(1-phenylethyl)amino]-5-oxopentanoic acid A solution of Part B anhydride (7.32 g, 30.0 mmole) in dry toluene (120 ml) was cooled to −78° C. (dry ice-ethanol) under argon (some anhydride precipitated). To this mixture was added dropwise Et$_3$N (4.2 ml, 30.0 mmole) followed by S(−) α-methyl benzylamine (4.2 ml, 32.6 mmole). After stirring at −78° C. for 4.5 hours, the cooling bath was removed, the mixture allowed to warm to room temperature, and stirred for one hour. The mixture was partitioned between ethyl acetate (100 ml)-tetrahydrofuran (THF) (50 ml)/5% KHSO$_4$ (175 ml). The organic phase was washed with 5% KHSO$_4$ and saturated NaCl solutions, dried over Na$_2$SO$_4$ and evaporated to give crude title acid compound as a white semi-solid. Esterification of a 25 mg sample of the crude product with CH$_2$N$_2$ gave a 79:21 mixture of (3S,1'S): (3R,1'S) methylesters as determined by $^1$H-NMR (270 MHz, CD$_3$CN).

TLC:(ethyl ether-hexane; 2:1) R$_f$=0.37 (major, 3S,1'S), 0.29 (minor, 3R,1'S). $^1$H-NMR (3S,1'S) δ0.08 ppm (3H,S), 0.10 (3H,S), 0.86 (9H,S). $^1$H-NMR (3R,1'S) δ0.03 ppm (3H,S), 0.06 (3H,S), 0.79 (9H,S).

The crude acid was triturated with cold ethyl ether to give (3S,1'S)-3-[[(1,1-dimethylethyl)dimethylsilyl]oxy]-5-[(1-phenylethyl)amino]-5-oxopentanoic acid (8.160 g, 74.5%) as white crystals which showed only a trace of the 3R,1'S-isomer after esterification with CH$_2$N$_2$. Evaporation of the mother liquor gave 2.756 g of the 3R,1'S-isomer as a thick oil.

The above experiment was repeated exactly as above to give (3S,1'S)-3-[[(1,1-dimethylethyl)dimethylsilyl]oxy]-5-[(1-phenylethyl)amino]-5-oxopentanoic acid (8.275 g, 76%) and (3R,1'S)-3-[[(1,1-dimethylethyl)dimethylsilyl]oxy]-5-[(1-phenylethyl)amino]-5-oxopentanoic acid (2.654 g). The two batches of the crystalline isomer (total: 16.435 g) were combined and recrystallized from ethyl acetate-hexane to give pure (3S,1'S)-3-[[(1,1-dimethylethyl)dimethylsilyl]oxy]-5-[(1-phenylethyl)amino]-5-oxopentanoic acid (15.790 g, 72%) as white plates, m.p. 175.5°–176.5° C. [α]$_D$=−68.4° (c=1.02, CH$_3$OH). Esterification of the recrystallized material with CH$_2$N$_2$ showed no trace of the 3R,1'S-isomer by TLC or 270 MHz NMR.

D.
(3S,1'S)-3-[[(1,1-Dimethylethyl)dimethylsilyl]oxy]-5-[(1-phenylethyl)amino]-5-oxopentanoic acid, methyl ester A solution of Part C acid (15.365 g, 42.1 mmole) in dry dimethylformamide (DMF) (50 ml) was treated with powdered KHCO$_3$ (6.30 g, 63.0 mmole) and methyl iodide (3.90 ml, 62.6 mmole) and stirred at room temperature under argon for 18 hours. The mixture was then partitioned between ethyl acetate (250 ml) and H$_2$O (150 ml); the organic phase was washed with H$_2$O (3×75 ml) and saturated NaCl solution, dried over Na$_2$SO$_4$ and evaporated to give crude title amide ester (16.56 g, theory: 15.95 g) as a colorless oil. TLC (ethyl ether:hexane; 2:1) single spot R$_f$=0.37.

E.
3-[[(1,1-Dimethylethyl)dimethylsilyl]oxy]pentanedioic acid, monomethyl ester A suspension of anhydrous sodium acetate (10.5 g, 128 mmole) in a solution of crude Part D amide-ester (16.56 g, theory: 15.95 g, 42.1 mmole) in dry CCl$_4$ (100 ml) at 0° C. (ice bath) under argon was treated with 7.8M N$_2$O$_4$/CCl$_4$ (75 ml, prepared by passing N$_2$O$_4$ in CCl$_4$ at 0° C., concentration determined iodometrically) in ~20 ml portions. After stirring at 0° C. for 3 hours, the cold mixture was partitioned between CH$_2$Cl$_2$-ice/H$_2$O. The organic phase was dried over Na$_2$SO$_4$ and evaporated at room temperature to give the crude N-nitrosoamide as a bright yellow oil. TLC (ethyl ether-hexane; 2:1) R$_f$=0.79.

The crude N-nitrosoamide was immediately taken up in dioxane (100 ml) and heated to 65°–75° C. (bath temperature) under argon for 2.5 hours. Vigorous N$_2$ evolution was observed and the yellow color of the solution gradually faded until the solution was nearly colorless. Evaporation of the solution gave a ~1:1 mixture of title acid and its corresponding α-methylbenzyl ester. TLC (CH$_2$Cl$_2$-hexane; 3:1) R$_f$ (acid)=0.05, R$_f$ (ester)=0.37. (R$_f$ of N-nitrosoamide=0.56).

The mixture of title acid and its α-methylbenzyl ester was taken up in CH$_3$OH (100 ml), treated with 20% Pd(OH)$_2$-C (1.0 g) and stirred under an H$_2$ atmosphere (balloon) for 2 hours. The mixture was filtered through Celite and evaporated to dryness to give crude title acid (11.6 g, 100%) as a colorless oil which solidified in the refrigerator. TLC (CH$_3$OH-CH$_2$Cl$_2$; 1:9) R$_f$ 0.51.

F.
(R)-6-(Dimethoxyphosphinyl)-3-[[(1,1-dimethylethyl)dimethylsilyl]oxy]-5-oxohexanoic acid, methyl ester To a solution of dimethyl methylphosphonate (18.8 g, 152 mmole) in dry THF (200 ml) at −78° C. under argon was added 1.6M n-butyllithium/hexane (92 ml, 147 mmole) via syringe over a period of 10 minutes. The resulting mixture was stirred at −78° C. for 45 minutes, during which time a white precipitate developed. To the resulting solution was added a solution of the Part E crude acid (11.6 g, 42 mmole) in THF (50 ml) dropwise over a period of ~15 minutes. The resulting mixture was stirred at −78° C. for 1 hour and then quenched by the dropwise addition of saturated NH$_4$Cl solution (20 ml). The mixture was allowed to warm to room temperature and partitioned between ethyl acetate-5% KHSO$_4$. The organic phase was washed with saturated NaCl solution, dried over Na$_2$SO$_4$ and evaporated to give the crude keto-phosphonate acid as a colorless oil. TLC (CH$_3$OH—CH$_2$Cl$_2$; 1:9) R$_f$=0.44 (R$_f$ of Part E acid=0.51).

A solution of the crude acid in ethyl ether (75 ml) at 0° C. (ice bath) was treated with CH$_2$N$_2$/ethyl ether (prepared from 15.0 g 1-methyl-3-nitro-1-nitrosoguanidine (MNNG), 50 ml 40% KOH/150 ml ethyl ether) in portions until the yellow color of excess CH$_2$N$_2$ persisted. Acetic acid was added to discharge the excess CH$_2$N$_2$ and the solution was evaporated to dryness. The crude methyl ester was purified by flash chromatography on Whatman LPS-1 silica gel (150 g) eluting with acetone-hexane (2:8) to give pure title keto-phosphonate (10.521 g, 65% overall from Part C acid) as a pale yellow, viscous oil. TLC: (acetone-hexane; 4:6) R$_f$=0.31. $^1$H-NMR (270 MHz, CD$_3$CN) 0.0 ppm (6H,S), 0.78 (9H,S), 2.33 (1H, q, J=15, 7 Hz), 2.48 (1H, q, J=15, 5 Hz), 2.80 (2H, septet), 3.06 (2H, d, J=23 Hz), 3.56 (3H,S), 3.64 (6H, d, J=11 Hz), 4.46 (1H, quintet, J=5–6 Hz).

What is claimed is:

1. A process for preparing a keto-phosphonate which comprises reacting an anhydride of the structure

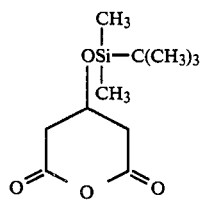

with S-α-methylbenzylamine to form a mixture of amides, separating the amide

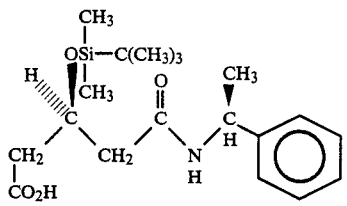

and reacting the said amide with an alkyl halide in the presence of a base to form the corresponding amide ester of the structure

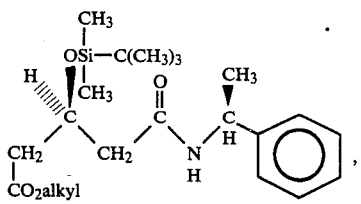

treating the amide ester with dinitrogen tetroxide, heating the resulting N-nitrosoamide and treating the product with hydrogen in the presence of a catalyst to form the acid of the structure

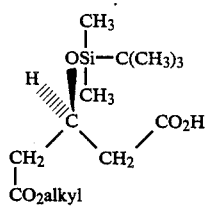

and treating said acid with dimethyl methylphosphonate and n-butyllithium to form the ketophosphonate

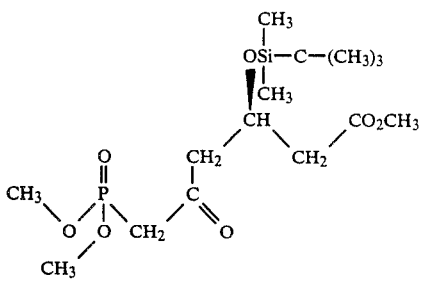

2. The process as defined in claim 1 wherein reaction of the anhydride and S-α-methylbenzylamine is carried out in the presence of a weak base and an inert organic solvent.

3. The process as defined in claim 2 wherein the anhydride and S-α-methylbenzylamine are reacted under a reduced temperature of within the range of from about −100° to about 0° C.

4. The process as defined in claim 1 wherein the alkyl halide employed to esterify the amide is methyl iodide and the esterification is carried out in the presence of a weak base and an inert organic solvent.

5. The process as defined in claim 1 wherein the reaction of the amide ester with dinitrogen tetroxide is carried out in the presence of anhydrous sodium acetate to form the corresponding N-nitrosoamide and the N-nitrosoamide is taken up in dioxane and heated under an inert atmosphere to release $N_2$ and form a mixture of the acid

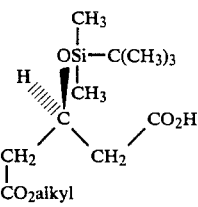

and its corresponding α-methylbenzyl ester.

6. The process as defined in claim 5 including the step of treating said mixture of said acid and 2-methylbenzyl ester with hydrogen in the presence of a hydrogenation catalyst to form said acid.

7. The process as defined in claim 6 wherein said acid is treated with dimethyl methylphosphonate and n-butyllithium at a reduced temperature within the range of from about −100° to about −50° C.

* * * * *